(12) United States Patent
Erman et al.

(10) Patent No.: US 7,482,378 B2
(45) Date of Patent: Jan. 27, 2009

(54) PHYSIOLOGICAL COOLING COMPOSITIONS

(75) Inventors: Mark B. Erman, Atlantic Beach, FL (US); Patrick J. Whelan, Fernandina Beach, FL (US); Joe W. Snow, Kingsland, GA (US)

(73) Assignee: Millenium Specialty Chemicals, Inc., Houston, TX (US)

( * ) Notice: Subject to any disclaimer, the term of this patent is extended or adjusted under 35 U.S.C. 154(b) by 281 days.

(21) Appl. No.: 10/857,272

(22) Filed: May 28, 2004

(65) Prior Publication Data

US 2005/0265930 A1    Dec. 1, 2005

(51) Int. Cl.
*A61K 31/16* (2006.01)
*A61K 8/00* (2006.01)
*C07C 233/00* (2006.01)

(52) U.S. Cl. .................. 514/613; 424/49; 424/434; 424/435; 514/506; 514/513; 514/625; 514/630

(58) Field of Classification Search ............... None
See application file for complete search history.

(56) References Cited

U.S. PATENT DOCUMENTS

| | | | | |
|---|---|---|---|---|
| 5,451,404 | A * | 9/1995 | Furman | 424/401 |
| 5,843,466 | A * | 12/1998 | Mane et al. | 424/401 |
| 5,993,836 | A * | 11/1999 | Castillo | 424/401 |
| 6,277,385 | B1 * | 8/2001 | Luke | 424/401 |
| 6,280,762 | B1 | 8/2001 | Bealin-Kelly et al. | 424/401 |
| 6,303,817 | B1 | 10/2001 | Boden et al. | 564/129 |
| 6,306,429 | B1 | 10/2001 | Bealin-Kelly | 424/439 |
| 6,319,513 | B1 | 11/2001 | Dobrozsi | 424/434 |
| 6,344,218 | B1 | 2/2002 | Dodd et al. | 424/605 |
| 6,350,438 | B1 | 2/2002 | Witt et al. | 424/53 |
| 6,355,706 | B1 | 3/2002 | Rajaiah | 523/120 |
| 6,391,886 | B1 | 5/2002 | Lee | 514/289 |
| 6,432,441 | B1 | 8/2002 | Bealin-Kelly et al. | 424/440 |
| 6,475,497 | B1 | 11/2002 | Rajaiah et al. | 424/401 |
| 6,475,498 | B1 | 11/2002 | Rajaiah et al. | 424/401 |
| 6,482,983 | B1 | 11/2002 | Lebedev et al. | 564/129 |
| 6,500,406 | B1 | 12/2002 | Rajaiah et al. | 424/49 |
| 6,509,007 | B2 | 1/2003 | Rajaiah et al. | 424/53 |
| 6,550,474 | B1 | 4/2003 | Anderson et al. | 128/200.24 |
| 6,627,233 | B1 * | 9/2003 | Wolf et al. | 426/3 |
| 6,638,521 | B2 | 10/2003 | Dobrozsi | 424/434 |
| 6,649,178 | B2 | 11/2003 | Mohammadi et al. | 424/401 |
| 6,703,000 | B2 | 3/2004 | Ning et al. | 424/58 |
| 6,706,277 | B2 | 3/2004 | Day et al. | 424/440 |
| 2004/0082654 | A1 * | 4/2004 | Pesce et al. | 514/547 |

FOREIGN PATENT DOCUMENTS

| | | |
|---|---|---|
| DE | 2205255 | 2/1971 |
| DE | 2317538 | 7/1973 |
| DE | 2413639 | 3/1974 |
| GB | 1351761 | 2/1971 |
| GB | 1421744 | 2/1972 |
| GB | 1421743 | 4/1972 |
| GB | 1422998 | 3/1973 |
| WO | WO93/23005 | * 11/1993 |
| WO | WO 02/051392 | 7/2002 |
| WO | WO 03/011816 | 2/2003 |
| WO | WO 2004/037764 | 5/2004 |

OTHER PUBLICATIONS http://www.leffingwell.com/cooler_than_menthol.htm p. 2.*
Wang et al. "Eutectic Composition of a Chiral Mixture Containing a Racemic Compound", Organic Process Research and Development, 9 pp. 670-676, 2005.*
Jacobs and Johncock, "Some like it cool: Menthol derivatives as effective cosmetic cooling agents:results of a worldwide study." Perfümerie und kosmetik, 80. Jahrgang Nr. Apr. 1999 pp. 26-31.
H&R Frescolat Cooling Ingredients 12 pages.
H&R Frescolat ML cryst. Cooling Agent (oil-soluble) 2 pages.

* cited by examiner

*Primary Examiner*—Frederick Krass
*Assistant Examiner*—Lezah W Roberts
(74) *Attorney, Agent, or Firm*—Jonathan L. Schuchardt

(57) ABSTRACT

The present invention provides, in one aspect, a physiological cooling composition comprising at least one cyclohexane carboxamide, at least one acyclic carboxamide, and at least one stereoisomer of menthyl lactate. In another aspect, disclosed is a method for producing such composition. In still another aspect, disclosed are various consumer products comprising a physiological cooling composition comprising at least one cyclohexane carboxamide, at least one acyclic carboxamide, and at least one stereoisomer of menthyl lactate.

1 Claim, No Drawings

PHYSIOLOGICAL COOLING COMPOSITIONS

FIELD OF THE INVENTION

This invention relates generally to compounds possessing physiological cooling activity, compositions comprising these compounds and methods for the manufacture and use thereof.

BACKGROUND OF THE INVENTION

Physiological cooling agents, commonly known as coolants, continue to gain popularity for use in various consumer applications due to their recognized ability for improving desirable sensate properties in consumer products. The desired sensate properties are generally explained by the chemical action of such coolant compounds on the nerve endings responsible for the sensation of cold. Common applications and uses for these compounds include, but are not limited to foods, beverages, flavors, pharmaceuticals, perfumes, and miscellaneous cosmetic goods.

One of the most well-known physiological coolants is l-menthol, a compound having the structure shown below, and which has been widely used in several of the above mentioned applications. In particular, l-menthol has an excellent cooling strength, low sensitivity threshold, and is relatively inexpensive compared to other coolant compounds.

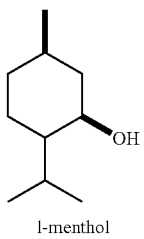

l-menthol

However, menthol also exhibits several undesirable properties, such as a strong "stinging" smell, a somewhat bitter taste, and it has a relatively high volatility. These disadvantages of l-menthol have limited its acceptance for use in various applications and therefore have stimulated intense research for suitable physiological cooling agents that possess a low volatility and exhibit a relatively weak odor or even no odor at all.

The primary focus of physiological coolant compound research has been toward the synthesis of compounds having a hydrocarbon skeleton similar to menthol, but which also comprise a "heavier" functional group than the hydroxyl functional group of menthol. As a result, a number of synthetic menthol substitutes have been developed and commercialized.

One commercially important group of synthetic coolants are the N-substituted 3-p-menthane carboxamides, commonly referred to as p-MCA and having the following structure:

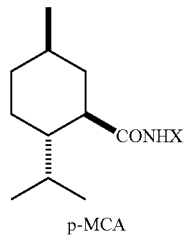

p-MCA

Originally disclosed by Wilkinson Sword Ltd., UK, in a number of patents world wide, i.e. GB 1,351,761, DE 2,205,255, U.S. Pat. No. 4,033,994, U.S. Pat. No. 4,136,163, and U.S. Pat. No. 4,150,052, N-substituted 3-p-menthane carboxamides p-MCA represent a larger group of cyclohexane carboxamides of the general structure 1:

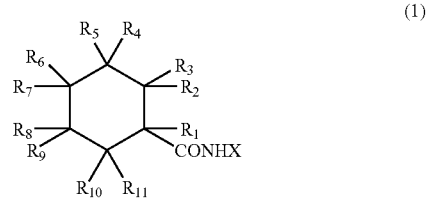

(1)

also disclosed by Wilkinson Sword Ltd. in DE 2,413,639, GB 1,422,998, U.S. Pat. No. 4,248,859 and U.S. Pat. No. 4,296,093. This larger group of cyclohexane carboxamides not only includes coolants having a carbon skeleton similar to menthol, but also coolants structurally unrelated to menthol.

A second commercially important group of synthetic coolants, and a group that is structurally unrelated to menthol, are the N-monosubstituted acyclic carboxamides of the general structure 2:

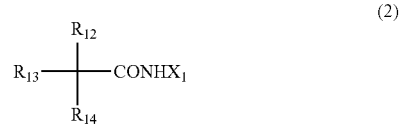

(2)

also first disclosed by Wilkinson Sword Ltd. in GB 1,421,743, GB 1,421,744, DE 2,317,538, and U.S. Pat. No. 4,153,679.

Substituents X and $X_1$ as referred to in general structures 1 and 2 above are typically lower linear or branched alkyl groups, such as methyl, ethyl, tertiary butyl; aryl groups such as p-methoxyphenyl; or functionally substituted alkyl groups such as ethoxycarbonylmethyl, and the like. Substituents $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$, as used in general structures 1 and 2 above, are typically independently hydrogen atoms, lower linear or branched alkyl groups, such as methyl, ethyl, isopropyl, tertiary butyl, and the like.

Commercially successful members of these two groups of synthetic physiological cooling agents are N-ethyl-3-p-menthane carboxamide (commonly referred to as WS-3) and N,2,3-trimethyl-2-isopropylbutanamide (commonly referred to as WS-23), both of which are available from Millennium Specialty Chemicals, Jacksonville, Fla.

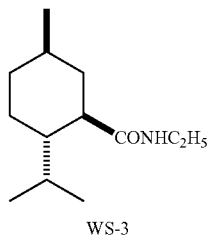 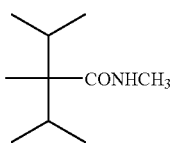

WS-3   WS-23

Other important carboxamide type physiological coolants include N-(ethoxycarbonylmethyl)-3-p-menthane carboxamide (WS-5) and N-tert-butyl-3-p-menthane carboxamide (WS-14).

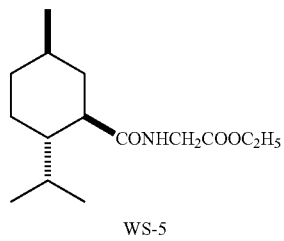 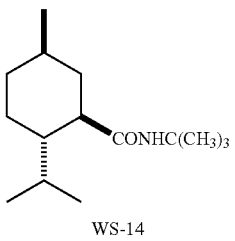

WS-5   WS-14

A third commercially important class of synthetic physiological cooling agents are l-menthol based esters and ethers, having the general structure:

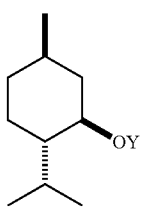

As used herein, substituent Y typically represents a lactic acid residue —OC(O)CH(OH)CH$_3$, a monosuccinate residue —OC(O)CH$_2$CH$_2$COOH, a monoglutarate residue —OC(O)CH$_2$CH$_2$CH$_2$COOH, or a glycerin residue —OCH$_2$CH(OH)CH$_2$OH, and the like. To date, the most commercially important representatives of this class have been menthyl lactate (ML) available from Symrise, Givaudan, and Millennium Specialty Chemicals; menthoxypropanediol (MPD) available from Takasago; monomenthyl succinate (MMS) available from V.Mane Fils, and monomenthyl glutarate (MMG). In general however, esters and ethers are weaker cooling agents compared to the above mentioned carboxamides. To that end, the most commercially important member of the ester/ether class is Menthyl Lactate ML.

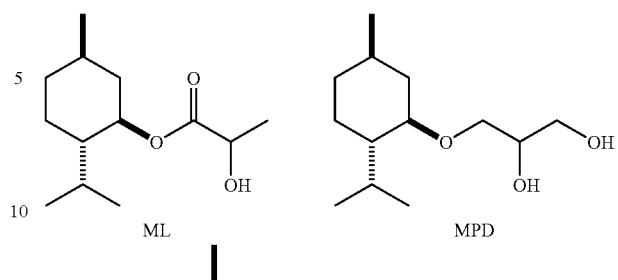

ML   MPD

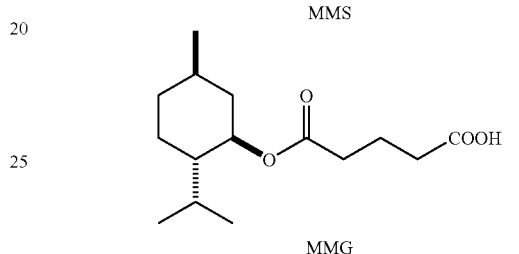

MMS

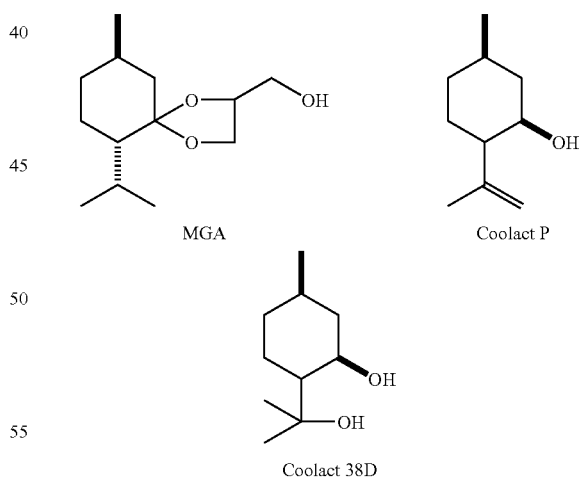

MMG

Lastly, menthone glycerin acetal (MGA) represents the commercially viable ketal group of synthetic coolants, and isopulegol (sold under the trade name Coolact® P) and p-menthane-3,8-diol (sold under the trade name Coolact® 38D) are two examples of the p-menthanol class of liquid coolants, both of which have also gained significant popularity as synthetic coolant compounds.

MGA   Coolact P

Coolact 38D

The spectrum of consumer products that incorporate physiological cooling agents continues to broaden and thus gives rise to a need for coolant compounds and compositions having more sophisticated and multifaceted physiological cooling properties. As a result, combinations of cooling agents are progressively attracting more attention. This trend is illustrated by numerous reports in the technical and patent literature, where several different coolants have been used in combination to arrive at a final consumer formulation.

Several attempts have been made to formulate compositions containing menthol and one or more synthetic coolant molecules. For example, U.S. Pat. Nos. 5,009,893 and 5,698,181 teach that combinations of l-menthol and p-menthane carboxamide in a chewing gum provide a long-lasting, breath-freshening perception without the bitterness of l-menthol taken alone. Similarly, U.S. Pat. No. 5,663,460 discloses that the organoleptic properties of a menthol composition improve when menthol is blended with pure isopulegol or with MPD.

Attempts have also been made to provide physiological cooling compositions that contain no menthol or at least insignificant amounts of menthol. These compositions are particularly desirable when the strong smell and taste of menthol have to be completely avoided. For example, U.S. Pat. Nos. 5,407,665, 5,681,549 and 5,686,063 teach combinations of MPD, WS-3 and WS-23, which are incorporated into a mouthwash composition together with an alkoxy or glycol ether and ethyl acetate or a polyhydric alcohol as co-solvents or solubilizers. Similarly, after shave lotions according to U.S. Pat. Nos. 5,449,512 and 5,527,530 contain WS-3 or WS-23, or mixtures thereof together with an alcohol and a low-molecular weight methylsiloxane or acyl lactylate.

Significantly, practically all physiological cooling agents of the carboxamide groups are solid materials at ambient temperature and atmospheric pressure, usually with relatively high melting points (see Table 1). A representative of the menthol-based esters and ethers group of physiological cooling agents, menthyl lactate (ML) is also a solid material, although with a relatively lower melting point (see Table 1). l-Menthol itself is a solid with a melting point of approximately 40-44° C. Several other commercial cooling agents listed above (MPD, MSS, MMG, MGA, Coolact P® and Coolact® 38D) exist as liquids at ambient temperature and atmospheric pressure.

TABLE 1

Melting points of commercially important solid cooling agents

| Trade name | Chemical name | Melting point, ° C. |
|---|---|---|
| l-Menthol | p-Menthan-3-ol | 40-44 |
| WS-3 | N-ethyl-3-p-menthane carboxamide | 97-101 |
| WS-5 | Substantially pure N-(ethoxycarbonylmethyl)-3-p-menthane carboxamide, same as N-[[5-methyl-2-(1-methylethyl)cyclohexyl]carbonyl]glycine | 80-82 |
| WS-14 | N-tert-butyl-3-p-menthane carboxamide | 147-150 |
| WS-23 | N,2,3-trimethyl-2-isopropyl butanamide | 60-62 |
| Menthyl Lactate | l-Menthyl ester of lactic acid | 40-45 |

In order to be added into a cooling composition, solid cooling agents must first be melted and dissolved in a flavor blend or dispersed in the emulsion. For example, the manufacturer's product literature on Menthyl Lactate (Frescolat® ML Crystal) from Symrise (former Haarmann & Reimer GmbH) advises that the product must be incorporated in a melted state into the oils, fragrances or emulsions at approximately 40-45° C. (Jacobs et al., Parfümerie und Kosmetik, 1999, Vol. 80, # 4, pp. 26-31). This added step of melting, of course, adds difficulties during the blending stage. This melting step, especially in the case of solid materials with higher melting points, such as WS-3, WS-5, and WS-14, also raises safety concerns. For example, a 25-kg pail of solid WS-3 with a melting point of about 100° C. or just below 100° C., must be placed in a "hot room," and heated to a temperature equal to or exceeding 100° C. In turn, the hot pail containing melted WS-3 has to be handled by personnel, introducing dangerous opportunities for burn related injuries to occur.

To that end, if the coolant is in the form of a free-flowing powder or crystalline form, it can be added to the composition as such. However, it is well-known that blending of a powder or crystalline material can cause inhomogeneity of the final blend. This is caused by an uneven distribution of the coolant, especially when the final blend is a solid, a semi-solid, or a viscous liquid. It also raises additional safety concerns due to the possible formation of explosive mixtures of the particulate dust and air. Therefore, additional attempts have been made to pre-dissolve the solid coolant agent in an additional food grade, flavor grade or pharmaceutical grade solvent such as ethanol or propylene glycol. However, as would be expected, the presence of an additional solvent in the final article is often undesirable. For example, with regard to propylene glycol, its presence in a final comestible article can impart an undesirable bitter taste nuance.

Currently, literature on solvent-free liquid compositions of physiological cooling agents is very limited. A recent pre-grant US Patent Application Publication 2004/0018954 (Su et al.) discloses that mixtures of l-menthol and menthyl lactate can be liquid under normal conditions, which is reasonably explained through a eutectic mixture. It should be noted that the best effect is achieved at 1:1 weight ratio, where the crystallization point of the mixture is 8.2° C. In the winter season, such mixtures would certainly solidify during shipping and the need for thawing or melting would still exist. Moreover, these mixtures are based on menthol as the major component which, as mentioned above, is often undesirable.

Therefore, there is still a need in the art for new and improved physiological cooling compositions comprising one or more carboxamide class cooling agents, wherein the composition is capable of existing as a liquid under normal or ambient conditions, even in the substantial absence of a solvent and even when all of the individual components of such composition exist as a solid at ambient temperature and atmospheric pressure, when taken separately.

SUMMARY OF THE INVENTION

The present invention is based, in part, upon physiological cooling compositions comprising at least one cyclohexane carboxamide; at least one acyclic carboxamide; and at least one stereoisomer of menthyl lactate.

Thus, in a first aspect, the present invention provides a physiological cooling composition, comprising a cyclohexane carboxamide having the general structure (1),

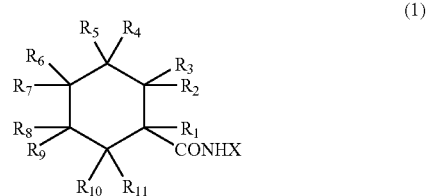

an acyclic carboxamide having the general structure (2),

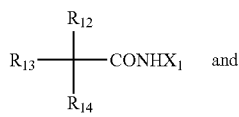

(2)

a stereoisomer of menthyl lactate, having the general structure ML,

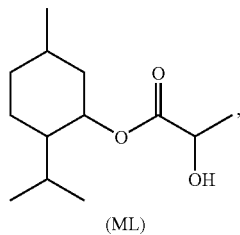

(ML)

wherein X and $X_1$ are independently a linear alkyl, a branched alkyl, an aryl, a functionally substituted aryl, an arylalkyl, a functionally substituted arylalkyl, or an alkoxycarbonylalkyl group; and wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently a hydrogen, a linear alkyl, a branched alkyl, an alkenyl, an alkoxy, an alkoxycarbonyl, or an alkoxycarbonylalkyl group.

In another aspect, the physiological cooling compositions of the instant invention are capable of existing in a stable liquid form at ambient temperature and atmospheric pressure, even in the substantial absence of a solvent and/or menthol.

In a third aspect, the present invention further provides a method for producing the physiological cooling compositions described herein. Accordingly, in one aspect, the method comprises the steps of a) providing at least one cyclohexane carboxamide of the general structure (1), at least one acyclic carboxamide of the general structure (2), and at least one stereoisomer of menthyl lactate of the formula (ML); and b) blending the at least one cyclohexane carboxamide, at least one acyclic carboxamide and at least one stereoisomer of menthyl lactate together under conditions effective to provide a physiological cooling composition as disclosed herein.

In a fourth aspect, the present invention provides the product produced by the process described herein.

In still another aspect, the present invention also provides a consumer product comprising the physiological cooling compositions described herein.

Additional advantages of the invention will be set forth in part in the description that follows, and in part will be obvious from the description, or may be learned by practice of the invention. To that end, the advantages of the invention will be realized and attained by means of the elements and combinations particularly pointed out in the appended examples and claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description, preferred embodiments of the invention and the Examples included therein. It is also to be understood that the various terminology used herein is for the purpose of describing particular embodiments only and is not intended to be limiting.

It should also be noted that, as used in the specification and the appended claims, the singular forms "a," "an" and "the" include plural referents unless the context clearly dictates otherwise. Thus, for example, reference to "a solvent" also includes mixtures of solvents.

Often, ranges are expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately," it will be understood that the particular value forms another embodiment. It will be further understood that the endpoints of each of the ranges are significant both in relation to the other endpoint, and independently of the other endpoint.

In this specification and in the claims that follow, reference will be made to a number of terms that shall be defined to have the following meanings:

As used herein, a "weight percent" or "percent by weight" of a component, unless specifically stated to the contrary, is based on the total weight of the formulation or composition in which the component is included.

As used herein, the term "optional" or "optionally" means that the subsequently described event or circumstance may or may not occur, and that the description includes instances where said event or circumstance occurs and instances where it does not.

As used herein, the term "alkyl" refers to a paraffinic hydrocarbon group which can be derived from an alkane by dropping one or more hydrogen(s) from the formula. Non-limiting examples include $C_1$-$C_{20}$ alkane derivatives such as methyl, ethyl, propyl, isopropyl, butyl, t-butyl, and isobutyl. To this end, it should be understood that an alkyl substituent suitable for use in the present invention can be a branched or straight chain alkyl substituent.

As used herein, the term "lower alkyl" refers to a $C_1$-$C_8$ alkyl group as defined above.

As used herein, the term "alkenyl" is intended to refer to a substituent derived from the class of unsaturated hydrocarbons having one or more double bonds. Those containing only one double bond are referred to as alkenes or alkenyl substituents. Those with two or more double bonds are called alkadienes (alkadienyl), alkatrienes (alkatrienyl) and so on. Non-limiting examples include ethenyl, propenyl, isopropenyl, butenyl, isooctenyl, and the like. To this end, it should be understood that an alkenyl substituent suitable for use in the present invention can be substituted or unsubstituted, including, without limitation, functional substituents.

As used herein, the term "aryl" refers to a compound or substituent whose molecules have the ring structure characteristic of benzene, naphthalene, phenanthrene, anthracene, and the like. That is to say, an aryl group typically contains either the 6-carbon ring of benzene or the condensed 6 carbon rings of other aromatic derivatives. For example, an aryl group can be a phenyl or naphthyl group. To this end, it should be understood that aryl substituents suitable for use with the present invention can be substituted or unsubstituted, including, without limitation, functional substituents.

As used herein, the term "alkoxy" refers to a functional group having the general structure —OR; wherein "R" is an alkyl group as defined herein.

As used herein, the term "alkoxycarbonyl" refers to a functional group having the general structure —(CO)—O—R, wherein "R" is an alkyl group as defined herein.

As used herein, the term alkoxycarbonylalkyl refers to a functional group having the general structure —R—(CO)—O—R, wherein "R" is an alkyl group as defined herein. A non-limiting example of the alkoxycarbonylalkyl group is —CH$_2$COOC$_2$H$_5$.

As used herein, the term "arylalkyl" refers to a group comprising an aryl group attached to an alkyl group. It should be understood, that both the alkyl group and the aryl group comprising the arylalkyl group can be substituted or unsubstituted, including, without limitation, functional substituents. A non-limiting example of the arylalkyl group is vanillyl group having the formula —CH$_2$C$_6$H$_3$(p-OH)(m-OMe).

As used herein, the term or phrase "effective," "effective amount," or "conditions effective to" refers to such amount or condition that is capable of performing the function or property for which an effective amount is expressed. As will be pointed out below, the exact amount or particular condition required will vary from one embodiment to another, depending on recognized variables such as the materials employed and the processing conditions observed. Thus, it is not always possible to specify an exact "effective amount" or "condition effective to." However, it should be understood that an appropriate effective amount will be readily determined by one of ordinary skill in the art using only routine experimentation.

As used herein, the phrase "functional substituent" or "functionally substituted" refers to substituents including, without limitation, carboxylic acid, acid anhydride, ester, acid halide, alkyl halide, halogen, amide, nitrile, aldehyde, ketone, alcohol or phenol, amine, and ether.

As summarized above, in a first aspect, the present invention provides a physiological cooling composition, comprising a cyclohexane carboxamide; an acyclic carboxamide; and a stereoisomer of menthyl lactate.

According to the invention, the cyclohexane carboxamide has the general structure (1),

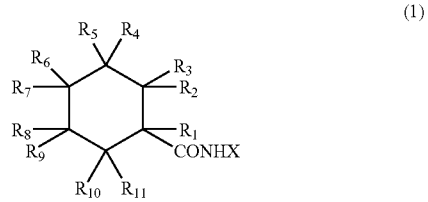

(1)

wherein X is a linear alkyl, a branched alkyl, an aryl, a functionally substituted aryl, an arylalkyl, a functionally substituted arylalkyl, or an alkoxycarbonylalkyl group. Further, R$_1$, R$_2$, R$_3$, R$_4$, R$_5$, R$_6$, R$_7$, R$_8$, R$_9$, R$_{10}$, and R$_{11}$, are each independently a hydrogen, a linear alkyl, a branched alkyl, an alkenyl, an alkoxy, an alkoxycarbonyl, or an alkoxycarbonylalkyl group. Accordingly, in a one aspect of the invention, the cyclohexane carboxamide is N-ethyl-3-p-menthane carboxamide, commonly known as WS-3 and having the general structure 1a:

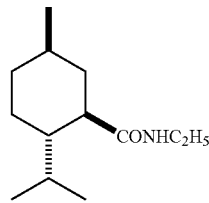

1a

In another aspect, the cyclohexane carboxamide is N-(ethoxycarbonylmethyl)-3-p-menthane carboxamide, also known as N-[[5-methyl-2-(1-methylethyl)cyclohexyl]-carbonyl]glycine or WS-5, and having the general structure 1b:

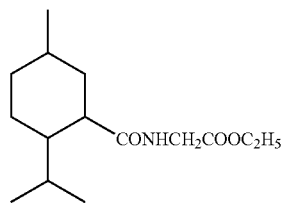

1b

To that end, the cyclohexane carboxamide 1b can be used in substantially pure form or less than substantially pure form. As used herein, substantially pure compound 1b can be at least 96% pure, 97% pure, 98% pure, 99% pure, 99% or even essentially 100% or pure form.

Purification of the impure ethyl ester of N-[[5-methyl-2-(1-methylethyl)cyclohexyl]carbonyl]glycine 1b can be performed using general purification methods known in the art for purifying an organic compound, which include, but are not limited to, crystallization, recrystallization, precipitation, redistillation, sublimation, or a combination thereof.

Additionally, compound 1b can also be used as a mixture of two or more stereoisomers or as practically pure isomers. In one aspect, it is preferred to use the (1R,2S,5R)-isomer, having the structure:

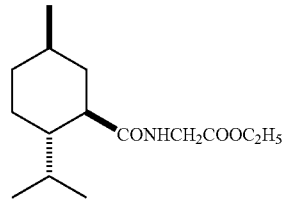

1b-(1R,2S,5R)

In still another aspect of the invention, the cyclohexane carboxamide is N-tert-butyl-3-p-menthane carboxamide, commonly known as WS-14, and having the structure 1c:

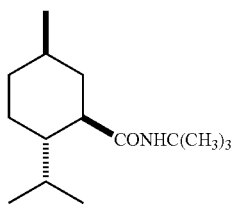

In another aspect of the invention, the cyclohexane carboxamide is a derivative of dihydrocyclogeranyl carboxamide having the general structure 1d,

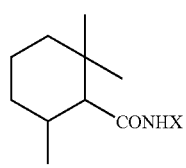

1d

Generally, cyclohexane carboxamide of the structure (1d) comprises a mixture of cis- and trans-isomers or it comprises individual cis- and trans-isomers of the structures 1d-cis and 1d-trans below:

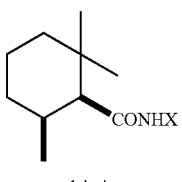 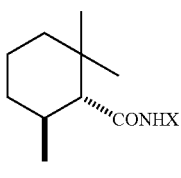

1d-cis          1d-trans

Suitable methods for obtaining cyclohexane carboxamides of the general formula 1d shown above include, without limitation, acid-catalyzed cyclization of geranyl nitrile into cyclogeranyl nitrile, and hydrogenation of the cyclogeranyl nitrile isomers into dihydrocyclogeranyl nitrites followed by a reaction of the dihydrocyclogeranyl nitrites with a suitable alkoxy-containing compound, for example an alkanol (X—OH) in the presence of an acid according to the following scheme:

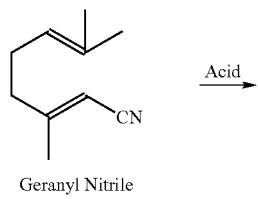

Geranyl Nitrile

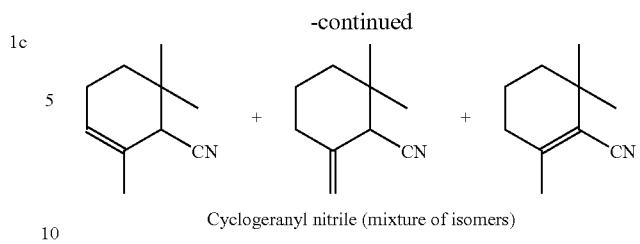

Cyclogeranyl nitrile (mixture of isomers)

↓ H₂/Cat

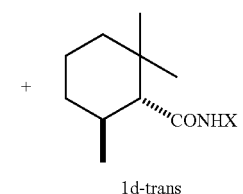

cis- and trans-Dihydrocyclogeranyl nitriles

↓ XOH / Acid

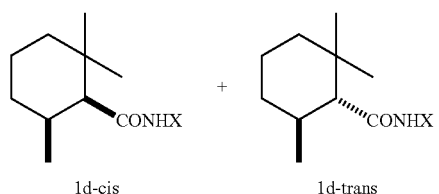

1d-cis          1d-trans

Alternatively, isomeric cyclogeranyl nitriles can be first converted to unsaturated cyclogeranyl amides and then hydrogenated to compounds of general formula 1d according to the scheme given below. Unsaturated cyclogeranyl amides shown on the scheme below also possess cooling activity and can be used instead of their saturated analogs as components of the blends.

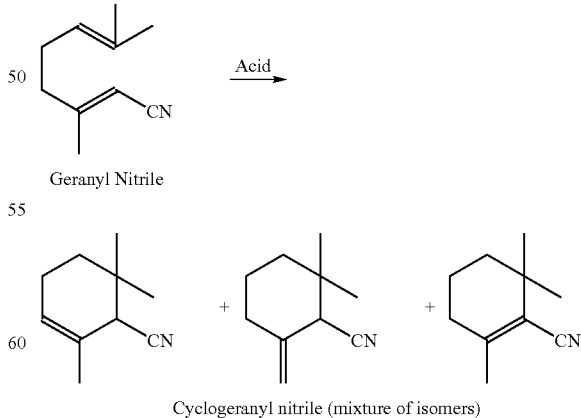

Geranyl Nitrile

Cyclogeranyl nitrile (mixture of isomers)

↓ XOH / Acid

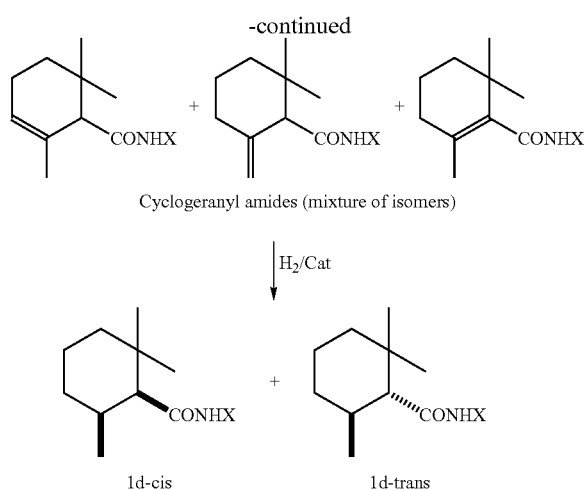

Cyclogeranyl amides (mixture of isomers)

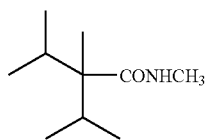

1d-cis    1d-trans

The at least one cyclohexane carboxamide, or mixture of cyclohexane carboxamides is preferably incorporated into the composition in an amount in the range of from about 4% by weight to about 90% by weight of the total physiological coolant composition, inclusive of all weight percentages and ranges therein. Accordingly, the at least one cyclohexane carboxamide can also be present in weight percentage amounts of about 5%, 10%, 15%, 20%, 25%, 30%, 35%, 40%, 45%, 50%, 55%, 60%, 65%, 70%, 75%, 80% or 85% by weight. The at least one cyclohexane carboxamide can also be present in a weight percentage amount in the range of from about 5%, 10%, 15%, 20%, 25%, 30%, 35%, 40%, 45%, 50%, 55%, 60%, 65%, 70%, 75%, 80% or 85% to about 10%, 15%, 20%, 25%, 30%, 35%, 40%, 45%, 50%, 55%, 60%, 65%, 70%, 75%, 80%, 85% or 90%. In still another aspect, the at least one cyclohexane carboxamide can be present in the range of from about 10% by weight to about 80% by weight, or from about 20% by weight to about 70% by weight, or even from about 30% by weight to about 60% by weight.

In one aspect, the acyclic carboxamide comprises N,2,3-trimethyl-2-isopropyl butanamide (also known as 2-(1-methylethyl)-N,2,3-trimethylbutanamide and having a trade name of WS-23) having the structure:

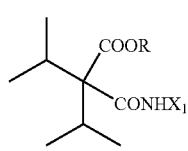

(2a)

In another aspect, the acyclic carboxamide according to the invention comprises a compound of the general structure 2b:

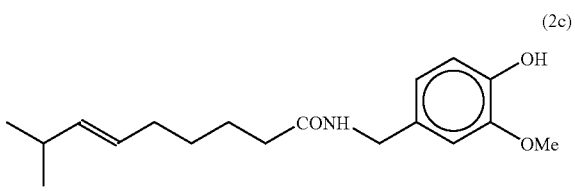

2b wherein the substituents $X_1$ and R are independently linear or branched alkyl groups as defined herein. One of ordinary skill in the art will appreciate that compounds of the general structure (2b) above can be obtained commercially, or for example, by a double alkylation of cyanoacetic esters with isopropyl bromide to give diisopropyl cyanoacetic ester, followed by a reaction with a suitable alkoxy-containing compound, for example an alkanol ($X_1$OH) in the presence of an acid according to the scheme:

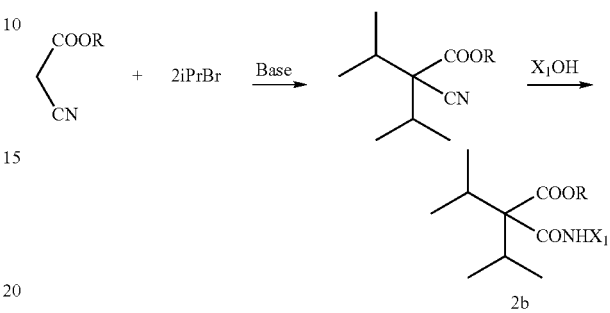

In one more aspect, the acyclic carboxamide according to the invention can comprise a compound of the structure 2c commonly known as capsaicin:

(2c)

[capsaicin structure]

Capsaicin is usually isolated from natural sources, wherein it is often present together with its dihydro derivative dihydrocapsaicin.

The at least one acyclic carboxamide, or a mixture of acyclic carboxamides is preferably incorporated into the composition in an amount in the range of from about 4% by weight to about 90% by weight of the total physiological coolant composition, inclusive of all weight percentages and ranges therein. Accordingly, the at least one acyclic carboxamide can also be present in weight percentage amounts of about 4%, 10%, 15%, 20%, 25%, 30%, 35%, 40%, 45%, 50%, 55%, 60%, 65%, 70%, 75%, 80% or 85% by weight. The at least one acyclic carboxamide can also be present in a weight percentage amount in the range of from about 5%, 10%, 15%, 20%, 25%, 30%, 35%, 40%, 45%, 50%, 55%, 60%, 65%, 70%, 75%, 80% or 85% to about 10%, 15%, 20%, 25%, 30%, 35%, 40%, 45%, 50%, 55%, 60%, 65%, 70%, 75%, 80%, 85% or 90%. In still another aspect, the acyclic carboxamide can be present in the range of from about 10% by weight to about 80% by weight, or from about 20% by weight to about 70% by weight, or even from about 30% by weight to about 60% by weight.

One of skill in the art will appreciate that the various carboxamides discussed herein are either commercially available or can be obtained through various known methods for preparing carboxamides. These methods are known in the art and, therefore, the reaction mechanisms for providing these carboxamides will not be discussed in detail herein. However, by way of reference, it should be understood that suitable methods can include, without limitation, the reaction of the corresponding carboxylic acid chloroanhydride with a corresponding primary amine such as that disclosed in DE 2,205,255; DE 2,317,538; GB 1,351,761; GB 1,421,744; U.S. Pat. No. 4,150,052; U.S. Pat. No. 4,178,459; U.S. Pat. No. 4,193,936; U.S. Pat. No. 4,226,988; and U.S. Pat. No. 4,230,688, the entire disclosures of which are hereby incorporated by reference for all purposes.

Additional suitable methods for the synthesis of carboxamides of the general formulas 1 and 2 include the reaction of a corresponding nitrile with a corresponding alkoxy-containing compound in the presence of an acid according to U.S. Pat. No. 6,482,983 and WO 2003/011816, the entire disclosures of which are also hereby incorporated by reference in their entirety for all purposes.

And still another suitable method for the synthesis of carboxamides of the general formulas 1 and 2 includes the reaction of a corresponding nitrile with a corresponding sulfate compound in the presence of an acid according to U.S. Pat. No. 6,303,817 and WO 2003/011816, the entire disclosures of which are hereby incorporated by reference for all purposes.

The physiological coolant compositions of the instant invention further comprise at least one stereoisomer of menthyl lactate, having the general structure (ML):

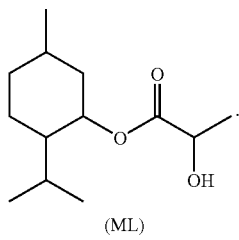

(ML)

In one aspect, the at least one menthyl lactate isomer is the 2S-(1R,2S,5R)-stereoisomer of the following structural formula ML-2S-(1R,2S,5R),

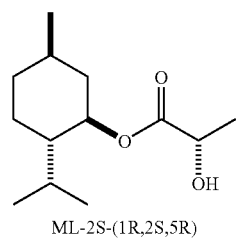

ML-2S-(1R,2S,5R)

Accordingly, the at least one menthyl lactate can comprise the ML-2S-(1R,2S,5R) in substantially chemically pure form, or, alternatively, can comprise this stereoisomer in combination with one or more additional stereoisomers of menthyl lactate. In still another aspect, compositions according to the invention comprise menthyl lactate of the formula ML as a mixture of its stereoisomers, but significantly enriched in the ML-2S-(1R,3R,4S) isomer.

The at least one menthyl lactate stereoisomer is preferably incorporated into the composition in an amount in the range of from about 4% by weight to about 90% by weight of the total physiological coolant composition, including all weight percentages and ranges therein. Accordingly, the menthyl lactate can also be present in weight percentage amounts of about 5%, 10%, 15%, 20%, 25%, 30%, 35%, 40%, 45%, 50%, 55%, 60%, 65%, 70%, 75%, 80% or 85% by weight. The at least one stereoisomer of menthyl lactate can also be present in a weight percentage amount in the range of from about 5%, 10%, 15%, 20%, 25%, 30%, 35%, 40%, 45%, 50%, 55%, 60%, 65%, 70%, 75%, 80% or 85% to about 10%, 15%, 20%, 25%, 30%, 35%, 40%, 45%, 50%, 55%, 60%, 65%, 70%, 75%, 80%, 85% or 90%. In still another aspect, the menthyl lactate can be present in the range of from about 10% by weight to about 80% by weight, or from about 20% by weight to about 70% by weight, or even from about 30% by weight to about 60% by weight.

One of ordinary skill in the art will appreciate that menthyl lactate is commercially available and can also be readily obtained by a synthesis reaction comprising a direct esterification of lactic acid with menthol followed by an aqueous work-up, as illustrated by the following reaction scheme.

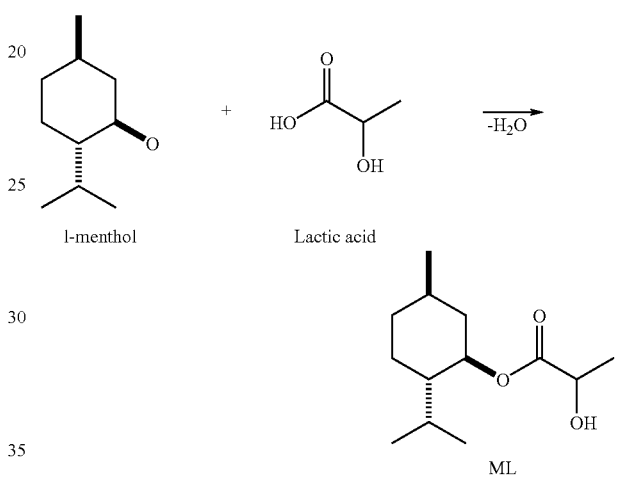

l-menthol    Lactic acid

ML

It should be understood that the physiological coolant compositions of the instant invention can comprise any desired combination of an at least one acyclic carboxamide, at least one cyclohexane carboxamide and at least one stereoisomer of menthyl lactate as disclosed herein. However, in one aspect, the at least one cyclohexane carboxamide comprises N-ethyl-3-p-menthane carboxamide (WS-3), the at least one acyclic carboxamide comprises N,2,3-trimethyl-2-isopropyl butanamide (WS-23), and the at least one menthyl lactate stereoisomer comprises ML-2S-(1R,2S,5R) stereoisomer of menthyl lactate.

In still another aspect, the physiological cooling compositions of the present invention exist as a stable liquid under normal or ambient conditions. As used herein, the term "normal conditions" refers to ambient temperature and atmospheric pressure at any given time. For example, in one aspect, ambient temperature is in the range of from approximately 19° C. to approximately 25° C. and all temperatures and ranges therein. It should however be appreciated that in another aspect, the liquid compositions according to the invention can be used in a spray-dried, co-dried, or microencapsulated form.

In still another aspect, the liquid composition remains a liquid under normal or ambient conditions upon inflicting a mechanical disturbance and/or seeding with crystals or powder of one or more individual components of the composition.

In still another aspect, the physiological cooling compositions of the instant application are substantially solvent free. As used herein, the term "substantially solvent free" refers to a physiological coolant composition that exists as a stable liquid under normal conditions irrespective of the presence of a solvent. That is to say that a solvent is not necessary in order for the physiological coolant composition to retain a liquid state under normal conditions. To that end, in one aspect, substantially solvent free can be a composition having no more than 10% by weight solvent. Alternatively, substantially solvent free can be a composition having less than 5% by weight solvent, or less than 2% by weight solvent; or less than 1% by weight solvent. In still another aspect, substantially solvent free can include a composition that does not contain any solvent.

However, although in one aspect the present invention provides cooling compositions that are free of solvents, the optional addition of a solvent to the liquid composition according to the invention does not constitute a departure from the invention. Non-limiting examples of solvents that can be added include alcohols such as ethyl alcohol and isopropanol, glycols such as propylene glycol and dipropylene glycol, glycerin, esters such as ethyl acetate, isopropyl myristate or triacetin, hydrocarbons such as heptane and petroleum fractions.

In still another aspect, the physiological cooling compositions of the instant invention are substantially menthol free. As used herein, the term "substantially menthol free" refers to a physiological coolant composition that does not contain a substantial amount of menthol. A substantial amount of menthol is defined in one aspect as an amount that would alter or influence the coolant properties of the composition. In another aspect, a substantial amount of menthol is defined as an amount that provides undesirable properties, such as a strong "stinging" smell, a somewhat bitter taste, or increased volatility. Accordingly, in one aspect, substantially menthol free refers to a composition comprising an amount of menthol that is less than or equal to about 10% by weight, or less than or equal to about 5% by weight, or less than or equal to about 3% by weight, or less than or equal to about 2% by weight, or less than or equal to about 1% by weight, or less than or equal to about 0.5% by weight or even about zero percent by weight.

However, the optional addition of menthol to the liquid composition according to the invention does not constitute a departure from the invention. It should also be noted that menthol can be present as a non-substantial impurity in commercial batches and samples of menthyl lactate. Accordingly, a non-substantial impurity, in one aspect, is an impurity present in an amount that is less than or equal to about 10% by weight, less than or equal to about 5% by weight, less than or equal to about 3% by weight, less than or equal to 2% by weight, less than or equal to 1% by weight, less than or equal to about 0.5% by weight or even about zero percent by weight. Therefore, in one aspect, the presence of a non-substantial amount of menthol in the composition according to the invention can be reasonably expected.

As illustrated by the appended examples, in another aspect, the compositions of the instant application surprisingly provide a synergistic cooling effect, i.e. a cooling strength of the mixture that noticeably exceeds a total of the individual cooling strengths of its components. This aspect can provide the added benefit of a potential cost savings by decreasing the necessary loading of the composition into a final blend an/or a consumer product.

In another aspect, the present invention further provides a method for producing the physiological cooling compositions described herein. Accordingly, in one aspect, the method comprises the steps of a) providing at least one cyclohexane carboxamide of the general structure (1), at least one acyclic carboxamide of the general structure (2), and at least one stereoisomer of menthyl lactate of the formula (ML); b) blending the at least one cyclohexane carboxamide, at least one acyclic carboxamide and at least one menthyl lactate together under conditions effective to provide a physiological cooling composition as disclosed herein.

In one aspect, the conditions effective to provide a physiological cooling composition comprise co-melting and/or kneading the mixture of the cyclohexane carboxamide, acyclic carboxamide and menthyl lactate to provide a liquid physiological cooling composition as disclosed herein. Alternatively, in another aspect, the individual components can be melted independently and then blended together in their respective liquid states to provide the physiological cooling composition.

In still another aspect, the compositions of the present invention can be used in any consumer good capable of using a cooling agent. In one aspect, the liquid compositions according to the invention are suitable for human consumption. In another aspect, the consumer goods are suitable for topical application to mammalian skin, including without limitation, human as well as veterinary applications. More specific examples of consumer goods include, without limitation, flavor blends, foods, cosmetic preparations, confectionery, soft and alcoholic beverages, chewing gums, toothpaste, dental floss, mouthwash, anti-plaque, anti-gingivitis compositions, shampoos, antidandruff shampoos, lotions, deodorants, after shave lotions, shaving gels, shaving aid composites, fragrances, skin sanitizing compositions, throat lozenges, throat drops, chewable antacid tablets, or pharmaceutical compositions or medications, including anti-inflammatory compositions, compositions for treatment of nasal symptoms, for upper gastrointestinal tract distress, for treating cold symptoms, for cough relief, for alleviating discomfort of hot flash, or for foot therapy, and the like.

It should also be understood that the compositions according to the instant invention can be used in combination with accessory compounds that facilitate the incorporation of the components of the composition into the above mentioned consumer goods. Examples of such accessory compounds include, but are not limited to, solvents such as ethanol or propylene glycol, control release agents or gel-forming agents, such as hydroxyalkyl cellulose or starch, modified starch, and various carriers such as amorphous silica, alumina, or activated carbon.

One of ordinary skill in the art would know how to incorporate the composition of the instant invention into a consumer good.

EXPERIMENTAL

The following examples are put forth so as to provide those of ordinary skill in the art with a complete disclosure and description of how the compositions according to the invention, and associated processes and methods are obtained, used, and/or evaluated, and are intended to be purely exemplary of the invention and are not intended to limit the scope of what the inventors regard as their invention. Efforts have been made to ensure accuracy with respect to numbers (e.g. amounts, temperature, etc.) and taste and cooling strength evaluations, but some errors and deviations should be accounted for. Unless indicated otherwise, parts are parts by weight, temperature is in ° C. (Celsius) or is at ambient temperature, and pressure is at or near atmospheric.

The aqueous solutions of products for organoleptic tests were obtained by dissolving appropriate amounts of the products in propylene glycol PG and adding the PG solution to an appropriate amount of water.

Comparative Examples 1-9

Dual Mixtures of WS-3 and Menthyl Lactate

Mixtures of WS-3 and menthyl lactate were prepared by co-melting given quantities of WS-3 and Menthyl Lactate and allowing them to cool to the ambient temperature in the laboratory (20-25° C.). The mixtures that did not spontaneously solidify were mechanically disturbed (shaken) for 0.5-3 minutes or seeded with WS-3 and/or ML. The results for Examples 1-9 are given in the Table 2 below.

TABLE 2

| Ex. No | Amount of WS-3, g (%) | Amount of ML, g (%) | Crystallized spontaneously | Crystallized upon shaking | Crystallized upon seeding |
|---|---|---|---|---|---|
| 1 | 2 (10) | 18 (90) | No | | Yes |
| 2 | 4 (20) | 16 (80) | No | | Yes |
| 3 | 6 (30) | 14 (70) | No | Yes | |
| 4 | 8 (40) | 12 (60) | No | Yes | |
| 5 | 10 (50) | 10 (50) | Yes | | |
| 6 | 12 (60) | 8 (40) | Yes | | |
| 7 | 14 (70) | 6 (30) | Yes | | |
| 8 | 16 (80) | 4 (20) | Yes | | |
| 9 | 18 (90) | 2 (10) | Yes | | |

Comparative Examples 10-18

Dual Mixtures of WS-23 and Menthyl Lactate

Mixtures of WS-23 and menthyl lactate were prepared by co-melting given quantities of WS-23 and Menthyl Lactate and allowing them to cool to the ambient temperature in the laboratory (20-25° C.). The mixtures that did not spontaneously solidify were mechanically disturbed (shaken) for 0.5-3 minutes or seeded with WS-23 and/or ML. The results are given in Table 3 below.

TABLE 3

| Ex. No | Amount of WS-23, g (%) | Amount of ML, g (%) | Crystallized spontaneously | Crystallized upon shaking | Crystallized upon seeding |
|---|---|---|---|---|---|
| 10 | 2 (10) | 18 (90) | No | | Yes |
| 11 | 4 (20) | 16 (80) | No | | Yes |
| 12 | 6 (30) | 14 (70) | No | | Yes |
| 13 | 8 (40) | 12 (60) | No | Yes, partially | |
| 14 | 10 (50) | 10 (50) | Yes, partially | | |
| 15 | 6 (60) | 4 (40) | Yes | | |
| 16 | 7 (70) | 3 (30) | Yes | | |
| 17 | 8 (80) | 2 (20) | Yes | | |
| 18 | 9 (90) | 1 (10) | Yes | | |

Comparative Examples 19-22

Solutions of WS-3 in MPD and WS-23 in MPD

Solutions of WS-3 in MPD or WS-23 in MPD were prepared by dissolving given quantities of WS-3 or WS-23 in MPD at elevated temperature and allowing them to cool to the ambient temperature in the laboratory (20-25° C.). The solutions that did not spontaneously solidify were seeded respectively with WS-3 or WS-23. The results are given in Table 4 below.

TABLE 4

| Ex. No | Amount of WS-3, g (%) | Amount of WS-23, g (%) | Amount of MPD, g (%) | Crystallized spontaneously | Crystallized upon seeding |
|---|---|---|---|---|---|
| 19 | 10 (50) | 0 | 10 (50) | No | Yes |
| 20 | 2.5 (20) | 0 | 10 (80) | No | Yes, partially |
| 21 | 0 | 10 (50) | 10 (50) | Yes, partially | |
| 22 | 0 | 2.5 (25) | 7.5 (75) | No | No |

Comparative Examples 23-26

Solutions of WS-3 in MMG and WS-23 in MMG

Solutions of WS-3 in MMG or WS-23 in MMG were prepared by dissolving given quantities of WS-3 or WS-23 in MMG at elevated temperature and allowing them to cool to the ambient temperature in the laboratory (20-25° C.). The solutions that did not spontaneously solidify were seeded respectively with WS-3 or WS-23. The results are given in Table 5 below.

TABLE 5

| Ex. No | Amount of WS-3, g (%) | Amount of WS-23, g (%) | Amount of MMG, g (%) | Crystallized spontaneously | Crystallized upon seeding |
|---|---|---|---|---|---|
| 23 | 10 (50) | 0 | 10 (50) | No | Yes |
| 24 | 2.5 (20) | 0 | 10 (80) | No | No |
| 25 | 0 | 10 (50) | 10 (50) | No | No |
| 26 | 0 | 2.5 (25) | 7.5 (75) | No | No |

Comparative Examples 27-29

Dual Mixtures of l-Menthol and Menthyl Lactate

Mixtures of l-menthol and menthyl lactate were prepared by co-melting given quantities of menthol and Menthyl Lactate and allowing them to cool to about 23° C. Then the mixtures were seeded with menthol and/or ML. Crystallization of a 50%:50% mixture required cooling with periodical seeding and solidified at +10.2° C., which is slightly higher than reported in US 2004/0018954 (+8.2° C.). The results are given in Table 6 below.

TABLE 6

| Ex. No | Amount of menthol, g (%) | Amount of ML, g (%) | Crystallized spontaneously | Crystallized upon seeding |
|---|---|---|---|---|
| 27 | 25 (25) | 75 (75) | No | Yes |
| 28 | 75 (75) | 25 (25) | No | Yes |
| 29 | 50 (50) | 50 (50) | No | Yes, but required deeper cooling to +10.2° C. |

Comparative Example 30

A Mixture of Two Cyclohexane Carboxamides and Menthyl Lactate in the Absence of an Acyclic Carboxamide A mixture of WS-3, menthyl lactate and N,2,2,6-Tetramethylcyclohexane-1-carboxamide was prepared by co-melting 5 g of WS-3, 5 g of Menthyl Lactate and 5 g of N,2,2,6-Tetramethylcyclohexane-1-carboxamide. Upon cooling to the ambient temperature in the lab, the mixture spontaneously solidified.

Inventive Examples 31-38

Compositions Comprising WS-3 as a cyclohexane carboxamide, WS-23 as an acyclic carboxamide, and ML Containing the ML-2S-(1R,2S,5R) stereoisomer Mixtures of WS-3, WS-23, and Menthyl Lactate were prepared by co-melting given quantities of WS-3, WS-23 and Menthyl Lactate and allowing them to cool to the ambient temperature in the laboratory (20-25° C.). The mixtures that did not spontaneously solidify were mechanically disturbed (shaken) for 0.5-3 minutes and/or seeded with WS-3, WS-23, and/or ML. The results are given in Table 7 below.

TABLE 7

| Ex. No | Amount of WS-3, g (%) | Amount of WS-23, g (%) | Amount of ML, g (%) | Liquid or solid at 21° C. | Liquid or solid upon shaking | Liquid or solid upon seeding |
|---|---|---|---|---|---|---|
| 31 | 5 (25) | 5 (25) | 10 (50) | Liquid | Liquid | Liquid |
| 32 | 6 (30) | 6 (30) | 8 (40) | Liquid | Liquid | Liquid |
| 33 | 10 (33.3) | 10 (33.3) | 10 (33.3) | Liquid | Liquid | Liquid |
| 34 | 7 (35) | 7 (35) | 6 (30) | Liquid | Liquid | Liquid |
| 35 | 21 (35) | 21 (35) | 18 (30) | Liquid | Liquid | Liquid |
| 36 | 48 (40) | 48 (40) | 24 (20) | Liquid | Liquid | Liquid |
| 37 | 4 (40) | 2 (20) | 4 (40) | Liquid | Liquid | Liquid |
| 38 | 18 (60) | 3 (10) | 9 (30) | Liquid | Liquid | Solid |

Inventive Example 39

Application of the Kneading Method for the Preparation of a Compositions Comprising WS-3 as a Cyclohexane Carboxamide, WS-23 as an Acyclic Carboxamide, and ML Containing the ML-2S-(1R,2S,5R) Stereoisomer A mixture of 18 g of WS-3, 18 g of WS-23, and 24 g of ML was kneaded over 12 hours in a rotating flask at room temperature and atmospheric pressure. The resulting composition was a clear transparent liquid and contained about 30% of WS-3, about 30% of WS-23, and about 40% of Menthyl Lactate.

Inventive Examples 40-43

Compositions Comprising WS-14 as a Cyclohexane Carboxamide, WS-23 as an Acyclic Carboxamide, and ML Containing the ML-2S-(1R,2S,5R) Stereoisomer Mixtures of WS-14, WS-23 and Menthyl Lactate were prepared by co-melting given quantities of WS-14, WS-23 and Menthyl Lactate and allowing them to cool to the ambient temperature in the laboratory (20-25° C.). The mixtures that did not spontaneously solidify were mechanically disturbed (shaken) for 0.5-3 minutes and/or seeded with WS-14, WS-23, and/or ML. The results are given in Table 8 below.

TABLE 8

| Ex. No | Amount of WS-14, g (%) | Amount of WS-23, g (%) | Amount of ML, g (%) | Liquid or solid at 21° C. | Liquid or solid upon shaking | Liquid or solid upon seeding |
|---|---|---|---|---|---|---|
| 40 | 5 (33.3) | 5 (33.3) | 5 (33.3) | Solid | | |
| 41 | 5 (27.8) | 6.5 (36.1) | 6.5 (36.1) | Liquid | Liquid | Solid |
| 42 | 5 (23.8) | 8 (38.1) | 8 (38.1) | Solid | | |
| 43 | 5 (20) | 8 (32) | 12 (48) | Liquid | Liquid | Liquid |

Inventive Example 44

Composition Comprising WS-5 as a Cyclohexane Carboxamide, WS-23 as an Acyclic Carboxamide, and ML Containing the ML-2S-(1R,2S,5R) Isomer Five grams of highly purified WS-5 (purity 99%+; melting point about 82° C.) was co-melted with equal amounts of WS-23 (5 g) and ML (5 g) to give 15 g of a clear transparent liquid composition containing about equal parts by weight of WS-5, of WS-23, and of Menthyl Lactate. After cooling the mixture to room temperature, the composition retained its liquid state at ambient temperature and at or near atmospheric pressure upon shaking and upon seeding with WS-5, WS-23 and ML.

Inventive Example 45

Composition Comprising WS-5 as a Cyclohexane Carboxamide, WS-23 as an Acyclic Carboxamide, ML, and an Additional Component, the Glyceryl Ether of p-menthane-3-carboxylic acid (WS-30)

Five grams of highly purified WS-5 (purity 99%+; melting point about 82° C.) was co-melted with 5 g of WS-23, 5 g of ML, and 5 g of Glyceryl ether of p-menthane-3-carboxylic acid (a liquid coolant also known in the art as WS-30) to give 20 g of a clear transparent liquid composition containing about 25% of WS-5, about 25% of WS-23, about 25% of Menthyl Lactate, and about 25% of WS-30. After cooling to room temperature, the composition retained its liquid state upon shaking and upon seeding with WS-5, WS-23 and ML.

Inventive Example 46

Composition Comprising WS-5 as a Cyclohexane Carboxamide, WS-23 as an Acyclic Carboxamide, ML, and an Additional Component, Monomenthyl Glutarate Five grams of highly purified WS-5 (purity 99%+; melting point about 82° C.) was co-melted with 5 g of WS-23, 5 g of ML, and 5 g of a liquid coolant Monomenthyl Glutarate (MMG) to give 20 g of a clear transparent liquid composition containing about 25% of WS-5, about 25% of WS-23, about 25% of Menthyl Lactate, and about 25% of MMG. After cooling the mixture to room temperature, the composition retained its liquid state upon shaking and upon seeding with WS-5, WS-23 and ML.

Inventive Example 47

Composition Comprising WS-5 as a Cyclohexane Carboxamide, WS-23 as an Acyclic Carboxamide, ML, and an Additional Component MPD Five grams of highly purified WS-5 (purity 99%+; melting point about 82° C.) was co-melted with 5 g of WS-23, 5 g of ML, and 5 g of a liquid coolant Menthoxy propanediol (MPD) to give 20 g of a clear transparent liquid composition containing about 25% of WS-5, about 25% of WS-23, about 25% of Menthyl Lactate, and about 25% of MPD. After cooling the composition to room temperature, the composition retained its liquid state upon shaking and upon seeding with WS-5, WS-23 and ML.

Inventive Examples 48-53

Compositions Comprising N,2,2,6-Tetramethylcyclohexane-1-carboxamide as a Cyclohexane Carboxamide, WS-23 as an Acyclic Carboxamide, and ML Containing the ML-2S-(1R,2S,5R) Isomer Mixtures of N,2,2,6-Tetramethylcyclohexane-1-carboxamide (melting point 146-148° C.) as the cyclic carboxamide, WS-23, and Menthyl Lactate were prepared by co-melting given quantities of N,2,2,6-Tetramethylcyclohexane-1-carboxamide, WS-23 and Menthyl Lactate and allowing them to cool to the ambient temperature in the laboratory (20-25° C.). The mixtures that did not spontaneously solidify were mechanically disturbed (shaken) for 0.5-3 minutes and/or seeded with WS-3, WS-23, and/or ML. The results are given in Table 9 below.

TABLE 9

| Ex. No | Amount of cyclohexane carboxamide g (%) | Amount of WS-23, g (%) | Amount of ML, g (%) | Liquid or solid at 21° C. | Liquid or solid upon shaking | Liquid or solid upon seeding |
|---|---|---|---|---|---|---|
| 48 | 5 (33.3) | 5 (33.3) | 5 (33.3) | Solid | | |
| 49 | 5 (25) | 5 (25) | 10 (50) | Liquid | Liquid | Solid |
| 50 | 2 (16.7) | 2 (16.7) | 8 (66.6) | Liquid | Liquid | Solid |
| 51 | 2 (16.6) | 3 (25) | 7 (58.3) | Liquid | Liquid | Solid |
| 52 | 1 (9.1) | 2 (18.2) | 8 (72.7) | Liquid | Liquid | Liquid |
| 53 | 1 (9.1) | 3 (27.3) | 7 (63.6) | Liquid | Liquid | Liquid |

Inventive Example 54

Composition Comprising WS-3 as a Cyclohexane Carboxamide, WS-23 as an Acyclic Carboxamide, Capsaicin as Additional Acyclic Carboxamide, and ML Containing the ML-2S-(1R,2S,5R) Stereoisomer Capsaicin, 0.1 g (from Aldrich), was added to 5 g of the blend obtained in Inventive Example 39 to give a clear solution. The solution retained its liquid state upon seeding with each of the individual components.

Inventive Examples 55-60

Illustration of Synergistic Cooling Effect of the Compositions of the Invention

A. Cooling strength values for individual coolants. Cooling strength values used in this invention for individual coolants were those generally accepted in the art and also additionally confirmed using expert evaluations conducted by Millennium Specialty Chemicals personnel on the basis of a sequential dilution method, i.e., a controlled dilution of samples to the concentration where their strength is about equal to the standard solution of WS-3. For purposes of Examples 55-60, a 10 ppm solution of WS-3 in water was used as the standard solution and was assigned a standardized cooling strength value of 10.0. The corresponding relative cooling strengths for the individual cooling agents were then assigned based upon an organoleptic determination of the approximate concentration of cooling agent that was required to provide about the same cooling strength as the standardized 10 ppm solution of WS-3.

Accordingly, the following cooling strengths were assigned to the cooling agents as follows: highly purified WS-5 had a relative cooling strength of about 16.7; WS-3 was assigned a cooling strength of 10.0; WS-23 had a relative cooling strength of about 5.0; Menthyl Lactate had a relative cooling strength of about 2.9; WS-14 had a relative cooling strength of about 5.0; WS-30 had a relative cooling strength of about 1.5, N,2,2,6-Tetramethylcyclohexane-1-carboxamide had a relative cooling strength of about 1.0, and MMG had a relative cooling strength of about 3.5.

B. Measurement of the cooling strength of the compositions. Aqueous solutions were prepared of compositions of coolants obtained in inventive examples 32, 35, 37, 44, 45, and 52. Each solution contained 10 ppm concentration of the total composition. These solutions were organoleptically tested using a scale from 0 (zero) to 10 of the cooling strength in comparison with the standard solution of 10 ppm of WS-3 in water, which was assigned a score of 10.0.

The mathematically expected scores (ES) were calculated according to the following formula:

$$(ES) = [CS_1(A\%:100) + CS_2(B\%:100) + CS_3(C\%:100)]$$

wherein $CS_1$, $CS_2$ and $CS_3$ represent the individual cooling strength for the cyclohexane carboxamide, acyclic carboxamide and menthyl lactate respectively, and wherein A %, B %, and C % represent the individual weight percentages for the cyclohexane carboxamide, acyclic carboxamide and menthyl lactate respectively present in the composition.

Comparative Results for various 10 ppm solutions of the compositions according to the invention are given in Table 10 below.

TABLE 10

| Ex. No | Composition according to Inventive Example # | Expected score based on strengths of individual components (ES) | Actual score (AS) | Synergy, % calculated as: (AS − ES):ES · 100% |
|---|---|---|---|---|
| 55 | 32 | 5.7 | 8 | 40.3 |
| 56 | 35 | 6.1 | 8 | 31.0 |
| 57 | 37 | 6.2 | 8 | 29.0 |
| 58 | 44 | 8.2 | 10 | 22.0 |
| 59 | 45 | 6.5 | 7 | 7.7 |
| 60 | 52 | 3.3 | 7 | 112.1 |

Throughout this application, various publications are referenced. The disclosures of these publications in their entireties are hereby incorporated by reference into this application.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A physiological cooling composition, consisting of:
   a) from 20 to 55 wt. % of a cyclohexane carboxamide selected from the group consisting of N-ethyl-3-p-menthane carboxamide, N-(ethoxycarbonylmethyl)-3-p-menthane carboxamide, and mixtures thereof;
   b) from 15 to 45 wt. % of N,2,3-trimethyl-2-isopropyl butanamide; and
   c) from 20 to 55 wt. % of menthyl lactate of the formula:

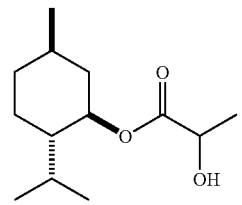

wherein the composition is a stable liquid at atmospheric pressure and a temperature within the range of 19° C. to 25° C.

* * * * *